(12) United States Patent
Proksa (10) Patent No.: US 8,229,060 B2
(45) Date of Patent: Jul. 24, 2012

(54) MEDICAL X-RAY EXAMINATION APPARATUS AND METHOD FOR K-EDGE IMAGING

(75) Inventor: Roland Proksa, Neu Wulmstorf (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/999,637

(22) PCT Filed: Jun. 17, 2009

(86) PCT No.: PCT/IB2009/052562
§ 371 (c)(1),
(2), (4) Date: Dec. 17, 2010

(87) PCT Pub. No.: WO2009/156898
PCT Pub. Date: Dec. 30, 2009

(65) Prior Publication Data
US 2011/0103550 A1    May 5, 2011

(30) Foreign Application Priority Data
Jun. 23, 2008 (EP) .................................... 08158745

(51) Int. Cl.
*A61B 6/00* (2006.01)
*G06K 9/00* (2006.01)
(52) U.S. Cl. ....... 378/5; 378/98.11; 378/98.12; 382/128
(58) Field of Classification Search ................ 378/4, 62, 378/70, 87, 5, 98.11, 98.12
See application file for complete search history.

(56) References Cited

U.S. PATENT DOCUMENTS

| | | | |
|---|---|---|---|
| 4,736,398 A | 4/1988 | Graeff et al. | |
| 4,887,604 A | 12/1989 | Shefer et al. | |
| 5,319,694 A | 6/1994 | Ingal et al. | |
| 5,987,095 A | 11/1999 | Chapman et al. | |
| 6,038,285 A | 3/2000 | Zhong et al. | |
| 7,187,753 B2 | 3/2007 | Freudenberger et al. | |

(Continued)

FOREIGN PATENT DOCUMENTS

| | | |
|---|---|---|
| DE | 102007017789 A1 | 10/2008 |
| WO | 2007034356 A2 | 3/2007 |

OTHER PUBLICATIONS

Elleaune et al: "Performance of Computed Tomography for Contrast Agent Concentration Measurements With Monochromatic X-Ray Beams: Comparison of K-Edge Versus Temporal Subtraction"; Physics in Medicine and Biology, 2002, vol. 47, pp. 3369-3385.

(Continued)

*Primary Examiner* — Edward Glick
*Assistant Examiner* — Alexander H Taningco (57) ABSTRACT

The present invention relates to a medical X-ray examination apparatus and method for performing k-edge imaging of an object of interest including material showing k-edge absorption. To allow the use of conventional detector technology, which does not suffer from the limitation to provide very high k-rate capabilities a method is proposed comprising the steps of: —emitting polychromatic X-ray radiation (4; 4*a*, 4*b*), —Bragg filtering said polychromatic X-ray radiation by a Bragg filter such that radiation (16) transmitted through said Bragg filter (14; 14*a*, 14*b*) passes through said object (5), —detecting X-ray radiation after passing through said object (5), —acquiring projection data at at least two different Bragg reflection angles of said Bragg filter (14; 14*a*, 14*b*), and —reconstructing a k-edge image from the acquired projection data.

20 Claims, 5 Drawing Sheets

U.S. PATENT DOCUMENTS

| | | | |
|---|---|---|---|
| 7,590,220 B1 * | 9/2009 | Lee et al. | 378/71 |
| 7,920,674 B2 * | 4/2011 | Kang et al. | 378/62 |
| 2004/0264644 A1 * | 12/2004 | Goebel et al. | 378/119 |
| 2008/0175350 A1 * | 7/2008 | MacDonald | 378/37 |

OTHER PUBLICATIONS

Dilmanian et al: "Tailoring X-Ray Beam Energy Spectrum to Enhance Image Quality of New Radiography Contrast Agents Based on Gd or Other Lanthanides"; Proceedings of SPIE, 2001, vol. 4320, 10 Page Document.

Zhong et al: "Monochromatic Energy-Subtraction Radiography Using a Rotating Anode Source and a Bent Laue Monochromator"; Physics in Medicine and Bioliolgy, 1997, vol. 42, pp. 1751-1762.

Zhong et al: "A Tunable Laue/Bent-Laue Monochromator With Fixed Second Crystal for Synchrotron Radiation"; AIP Conference Proceedings, 1997, vol. 417, pp. 95-100.

Freudenberger et al: "Perspectives of Medical X-Ray Imaging"; Nuclear Instruments & Methods in Physics Research—A: Accelerators, Spectrometers, Detectors and Associated Equipment, Elsevier, 2001, vol. 466, No. 1, pp. 99-104.

Suortti et al: "Performance Evaluation of a Bent Laue Monochromator"; Nuclear Instruments and Methods in Physics Research—A: Accelerators, Spectrometers, Detectors and Associated Equipment, Elsevier, 1990, vol. 297, pp. 268-274.

International Search Report for International Application PCT/IB2009/052562.

* cited by examiner

MEDICAL X-RAY EXAMINATION APPARATUS AND METHOD FOR K-EDGE IMAGING

FIELD OF THE INVENTION

The present invention relates to a medical X-ray examination apparatus and a corresponding method for performing k-edge imaging of an object of interest including material showing k-edge absorption.

BACKGROUND OF THE INVENTION

Conventional CT (Computed Tomography) imaging systems measure the X-ray attenuation and provide limited contrast for medical imaging. Most clinical applications use contrast agents to enhance the contrast. However, it would be desired to extend the information contents of CT imaging systems.

In k-edge imaging a tuneable, monochromatic source is used for detection of specific atoms by measuring the attenuation at two or more energies, generally before and behind the k-edge, which is, for instance, described in H. Elleaune, A. M. Charvet, S. Corde, F. Esteve and J. F. Le Bas, "Performance of computed tomography for contrast agent concentration measurements with monochromatic X-ray beams: comparison of k-edge versus temporal subtraction", Phys. Med. Biol. 47 (2002), 3369-3385. However, monochromatic sources are generally not suitable for clinical applications since they either have power levels far away from the required power for medical imaging or since they use synchrotron radiation of high energy accelerators.

WO 2007/034356 A2 discloses a CT imaging system using a conventional polychromatic X-ray source and an energy-resolving X-ray detector. With proper processing of the acquired data it is possible to reconstruct t least three images with a substance component (e.g. contrast agent component), a photo-effect component excluding the substance component and a Compton scatter component excluding the substance component. The X-ray detector provides a number of energy-resolved detection signals with spectral sensitivity for different energy bins, an energy bin being a section of the complete energy range in which said detection signal is available and of interest. The scanned object is then modelled as a combination of the photo-electric effect with a first spectrum, the Compton effect with a second spectrum and the substance with a k-edge in the interesting energy range with a third spectrum. The density length product for each of the components in each detection signal is modelled as a discrete linear system which is solved to obtain at least the k-edge components of said substance. From the k-edge components of said substance obtained for different detector positions a k-edge image of the substance can then be reconstructed with a conventional reconstruction method.

Spectral CT holds the potential to revolutionize CT imaging. Especially k-edge imaging will enable selective and quantitative imaging of targeted contrast materials. The major roadblock towards spectral CT, however, is the availability of detectors with very high count-rate capabilities.

SUMMARY OF THE INVENTION

It is an object of the present invention to provide a medical X-ray examination apparatus and a corresponding method for performing k-edge imaging of an object of interest including material showing k-edge absorption which allows the use of conventional detector technology, which does not suffer from the above described limitation to provide very high count-rate capabilities.

In a first aspect of the present invention a medical X-ray examination apparatus for performing k-edge imaging of an object of interest including material showing k-edge absorption is presented comprising:

a polychromatic X-ray source for emitting polychromatic X-ray radiation, a Bragg filter provided in the radiation path between said X-ray source and said object such that radiation transmitted through said Bragg filter passes through said object, a filter control unit for controlling the Bragg reflection angle of said Bragg filter, an X-ray detector for detecting X-ray radiation after passing through said object, an acquisition control unit for controlling the X-ray source, the X-ray detector and the filter control unit so as to acquire projection data at at least two different Bragg reflection angles of said Bragg filter, an image processing unit for reconstructing a k-edge image from the acquired projection data.

In a further aspect of the present invention a corresponding X-ray examination method is presented. Preferred embodiments of the invention are defined in the dependent claims.

The invention is based on the idea to use a conventional (polychromatic) X-ray source and a conventional X-ray detector for acquiring at least two sets of projection data. These projection data are acquired using radiation transmitted through a Bragg filter at different Bragg reflection angles. For instance, in a preferred embodiment, a first projection data set is acquired at a certain projection angle at a first Bragg reflection angle and a second projection data set is acquired (preferably at the same or substantially the same projection angle) at a second Bragg reflection angle. From the obtained projection data the desired k-edge image can be reconstructed. Such k-edge images are very desirable and allow, for instance, a direct measurement of a contrast agent such as Gd (or other contrast materials also showing a k-edge effect) injected into a patient.

According to a preferred embodiment said an acquisition control unit is adapted for controlling the X-ray source, the X-ray detector and the filter control unit so as to acquire projection data from different projection angles, wherein from substantially the same projection angle two sets of projection data are acquired at different Bragg reflection angles of said Bragg filter, and said imaging unit comprises:

a calculation unit for determining k-edge related projection data at said different Bragg reflection angles from the difference between said two sets of projection data acquired at substantially the same projection angle, and a reconstruction unit for reconstructing a k-edge image from said k-edge related projection data.

Thus, by comparing the two projection data sets obtained at different Bragg reflection angles a separation can be made between the attenuation effected by the material showing k-edge absorption and the absorption effected from other material in the examination zone/the object positioned there. Since the other material usually does not show such a sudden increase in the attenuation like the k-edge material this separation can be done by comparing the two projection data sets. The attenuation related to the k-edge material can be estimated or calculated and a k-edge image can be reconstructed there from.

It should be noted that the two sets of projection data obtained at different Bragg reflection angles should preferably be acquired at the same projection angle. However, in practice the gantry of a CT scanner is continuously rotating so that the X-ray source has moved a certain distance and angle between the acquisition of the first projection data set at the first Bragg reflection angle and the acquisition of the second projection data set at the second Bragg reflection angle. Hence, in practice these two projection data sets are acquired from substantially the same projection angle, which shall mean that the X-ray source has moved to a certain (small) extent between the two (preferably subsequent) measurements.

This might cause slight imaging errors, which can be corrected. For instance, the focal spot can be slightly changed between the two measurements, or the obtained projection data sets can be interpolated in an appropriate way.

According to an alternative embodiment said imaging unit comprises:

a reconstruction unit for reconstructing a first image from the projection data acquired at a first Bragg reflection angle and a second image from the projection data acquired at a second Bragg reflection angle, and a calculation unit for determining a k-edge image from the difference between said first and second images.

This embodiment has the advantage that it is not required that two projection data sets are obtained for at different Bragg reflection angles at the same or substantially the same projection angle. Further, no measures need to be taken for correction of imaging errors as with the above described embodiment.

In a further development thereof said acquisition control unit is adapted for controlling said filter control unit such that the two different Bragg reflection angles used during the acquisition of the two sets of projection data result in reflected radiation, the radiation reflected at a first Bragg reflection angle having a photon energy higher than a k-edge energy of a contrast agent present in the object and the radiation reflected at a second Bragg reflection angle having a photon energy lower than a k-edge energy of said contrast agent. Thus, according to this embodiment the dips in the spectrum of the radiation transmitted through the Bragg filter are preferably located at different sides of the k-edge. Preferably, the Bragg filter is controlled such that the dips in the spectra are located close to the k-edge since the k-edge material shows a significant difference of absorption at these locations so that the difference in the acquired projection data becomes unequal zero.

For control of the Bragg reflection angle the filter control unit is preferably adapted for controlling the position and/or orientation of the Bragg filter. However, there may be other ways to control the Bragg reflection angle. In an alternative embodiment the control unit is adapted for controlling the angle between said Bragg filter and said X-ray radiation emitted from the X-ray source. This angle is primarily responsible for changing the Bragg reflection angle.

In a simple embodiment the filter control unit comprises an actuator for controlling the position and/or orientation of the Bragg filter. There are various Bragg filters available which can be used according to the present invention. In a preferred embodiment the Bragg filter is curved to ensure that all radiation beams of the (fan-) beam emitted by the X-ray source exhibit the same Bragg reflection angle and show an identical spectrum. Generally, the Bragg filter can also be formed differently and/or located such that the reflection angle, under which incident X-ray radiation is reflected, is substantially constant for the entire X-ray radiation beam.

In a preferred embodiment the Bragg filter is a Highly Oriented Pyrolytic Graphite (HOPG) filter. Such a HOPG-filter has a certain spectral width and improves the sensitivity.

In a further aspect of the present invention an alternative solution of a medical X-ray examination apparatus for performing k-edge imaging of an object of interest including material showing k-edge absorption is presented solving the same problem comprising:

two polychromatic X-ray sources for emitting polychromatic X-ray radiation, two Bragg filters having different Bragg reflection angles, each of said Bragg filters being provided in a radiation path between one of said X-ray sources and said object such that radiation transmitted through said Bragg filters passes through said object, two X-ray detectors for detecting X-ray radiation after passing through said object, an acquisition control unit for controlling the X-ray sources and the X-ray detectors so as to acquire projection data from different projection angles, an image processing unit for reconstructing a k-edge image from the acquired projection data.

According to this aspect of the present invention the two projection data sets obtained at the two different Bragg reflection angles can be acquired simultaneously. Thus, the advantage of requiring more hardware elements compared to the apparatus according to the above explained first aspect is that the data acquisition requires less time.

As explained above for the apparatus of the first aspect, also this apparatus of the second aspect can be developed further by the same or similar embodiments.

Finally, in an aspect of the present invention a computer program is presented comprising program code means for controlling the claimed medical X-ray examination apparatus to perform the steps of the claimed medical X-ray examination method.

Preferably, the X-ray examination apparatus according to the present invention is used for the direct measurement of a contrast medium, such as a contrast agent used in medical imaging. This opens a number of new clinical features to CT imaging such as absolute blood volume measurement or cerebral perfusion imaging. It can enhance the contrast for angiography and allow the discrimination of the contrast agent filled lumen and calcified plaque within a vessel. Preferred contrast agents contain, for instance, iodine or, even more preferred due to a k-edge effect at a higher energy, gadolinium. The invention can further be applied in molecular imaging to reconstruct images showing a special substance, such as a special contrast agent, injected into a patient which only docks to certain cells or other targets, such as tumor cells or fibrin. The method according to the invention thus helps or can be used for quantitative measurements of such cells within a region of interest.

It shall be understood that the claimed apparatuses and the claimed method has similar and/or identical preferred embodiments as explained above and as defined in the dependent claims.

BRIEF DESCRIPTION OF THE DRAWINGS

These and other aspects of the invention will be apparent from and elucidated with reference to the embodiment(s) described hereinafter. In the following drawings

Like reference numbers refer in the Figures to identical or similar components.

DETAILED DESCRIPTION OF THE INVENTION

Figure 1:
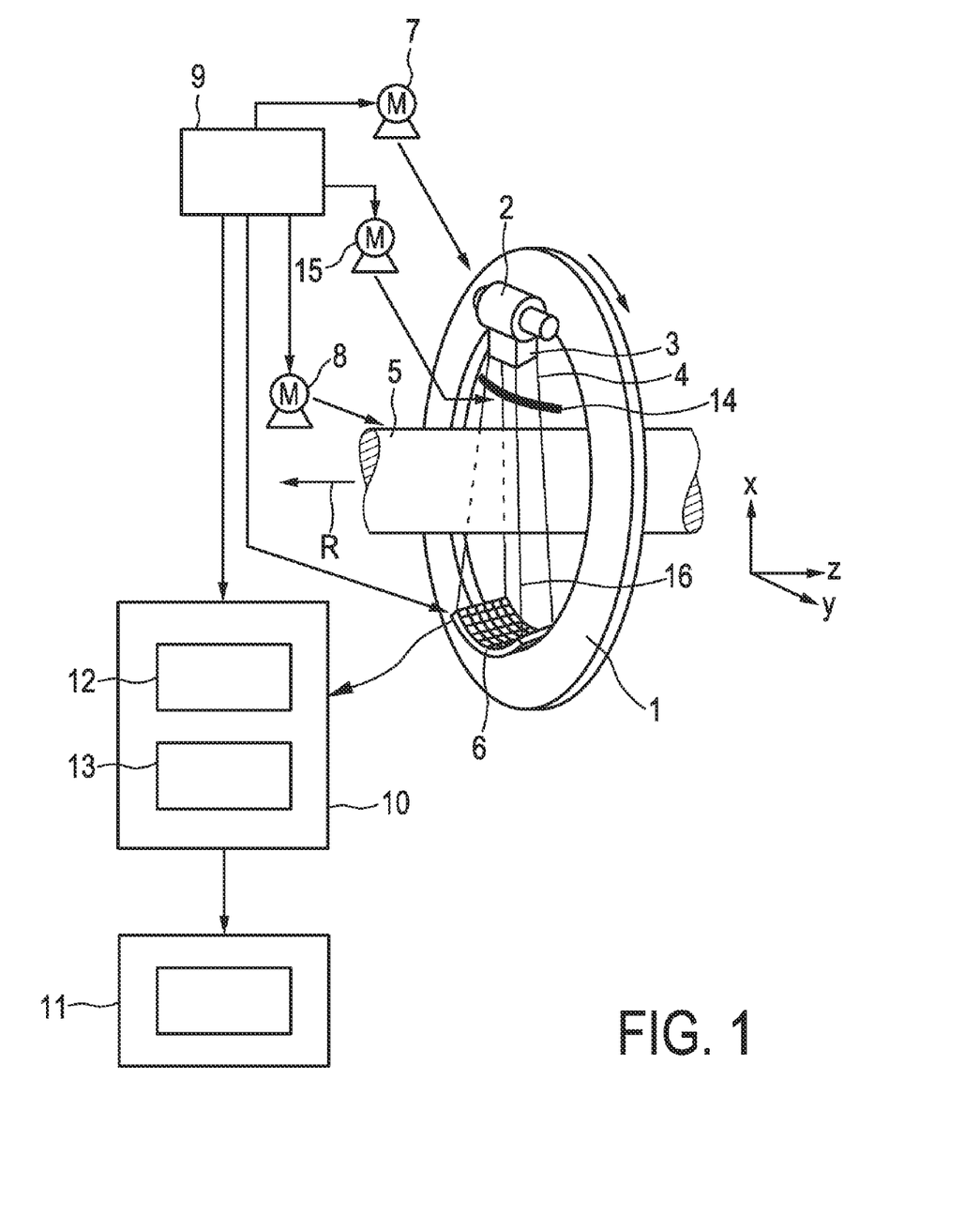
FIG. 1 shows a first embodiment of a medical X-ray examination apparatus according to the present invention.

FIG. 1 shows a first embodiment of a medical X-ray examination apparatus according to the present invention, in particular a CT imaging system. The CT imaging system shown in FIG. 1 includes a gantry 1 which is capable of rotation about an axis of rotation R which extends parallel to the z direction. The radiation source 2, in particular a (conventional) polychromatic X-ray tube for emitting a broad energy spectrum of X-rays, is mounted on the gantry 1. The X-ray tube 2 is provided with a collimator device 3 which forms a conical radiation beam 4 from the radiation produced by the X-ray tube 2. The radiation traverses an object (not shown), such as a patient, in a region of interest in a cylindrical examination zone 5. After having traversed the examination zone 5, the X-ray beam 4 is incident on an X-ray detector unit 6, in this embodiment a two-dimensional detector, which is mounted on the gantry 1.

The gantry 1 is driven at a preferably constant but adjustable angular speed by a motor 7. A further motor 8 is provided for displacing the object, e.g. the patient who is arranged on a patient table in the examination zone 5, parallel to the direction of the axis of rotation R or the z axis. These motors 7, 8 are controlled by a control unit 9, for instance such that the radiation source 2 and the examination zone 5 move relative to one another along a helical trajectory. However, it is also possible that the object or the examination zone 5 is not moved, but that only the X-ray source 2 is rotated.

The data acquired by the detector 6 are provided to an image processing device 1, which comprises a calculation unit 12 and a reconstruction unit 13, for image processing, in particular for reconstruction of a k-edge image of a substance, such as a contrast agent, in the object (e.g. the patient). Such a k-edge image is desired in clinical practice since it carries particular information and shows a high contrast in medical images and thus allows certain desired applications. The reconstructed image can finally be provided to a display 11 for displaying the image. Also the image processing device 10 is preferably controlled by the control unit 9.

Figure 2:
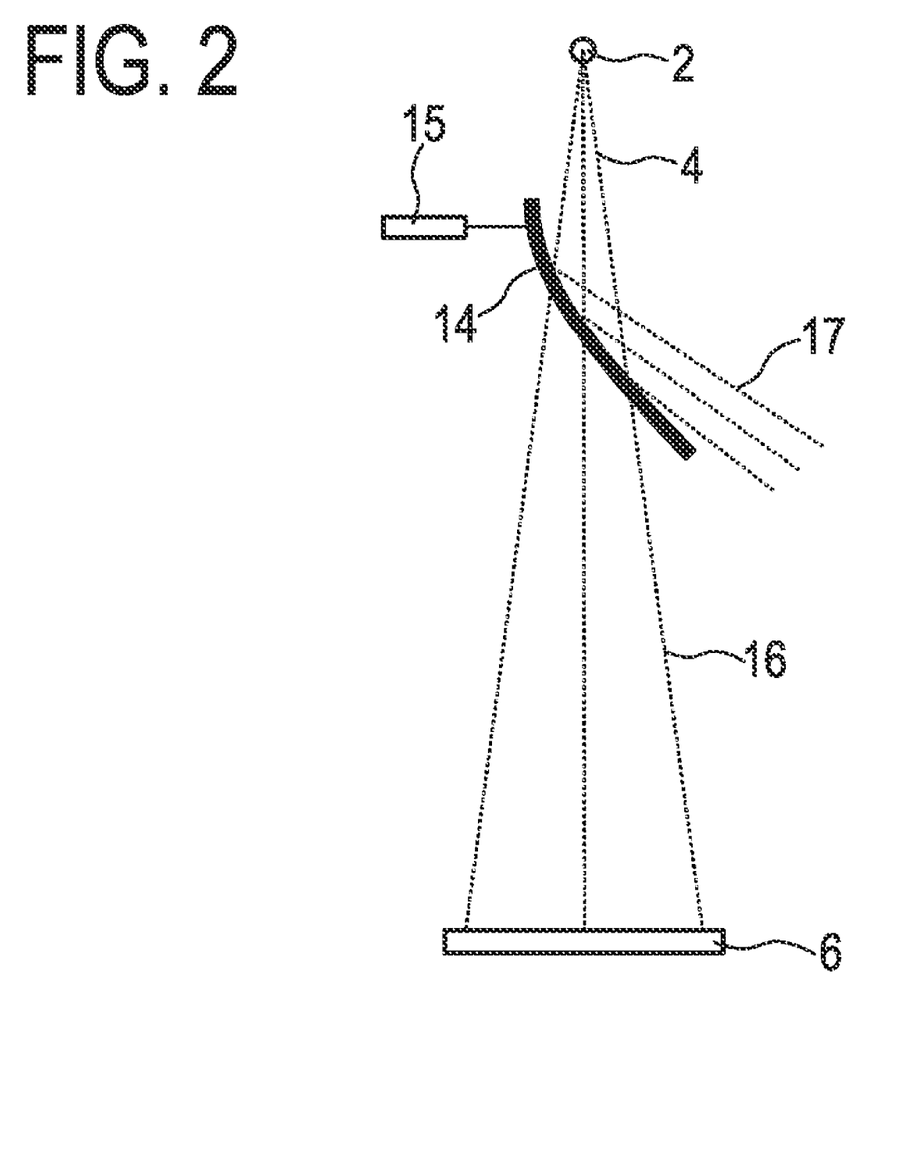
FIG. 2 illustrates the principle of the examination apparatus shown in FIG. 1.

According to this embodiment of the present invention, a Bragg filter 14 is provided in the radiation path between the X-ray source 2 and the object such that radiation 16 transmitted through said Bragg filter 14 passes through the object and that radiation 17 reflected by said Bragg filter 14 does not pass through the object. The reflected radiation 17 is not used according to the present invention (see also the enlarged diagram shown in FIG. 2 illustrating this principle).

Further, according to this embodiment of the present invention a filter control unit 15 is provided for control of the Bragg reflection angle of said Bragg filter 14. This filter control unit 15 can, for instance, be a simple actuator or other motor, by which the angle under which the Bragg filter 14 is placed in the radiation beam 4 can be changed. This filter control unit 15 is also controlled by the control unit 9, which preferably also controls the detector 6 for controlling the data acquisition by the detector 6.

When the radiation beam 4 hits the Bragg filter (crystal) 14 it reflects photons with wavelength λ and reflection angle Θ if the Bragg condition $n\lambda = 2d \sin \Theta$ is fulfilled, n being an arbitrary integer and d being the lattice parameter. While usually the reflected beam 17 is used for imaging, according to the present invention the transmitted beam 16 that lacks the reflected part 17 of the incident beam 4 is used. The transmitted beam 16 is then used as in a conventional CT imaging system.

By the additional actuator 15 the angle between the Bragg filter 14 and the X-ray beam 4 is dynamically controlled. Preferably, the Bragg filter 14 is curved such that for the entire beam 4 the reflection angle Θ stays constant.

Conventional Bragg crystals have a sharp reflection peak in the spectrum and reflect only a small fraction from a polychromatic beam. So-called HOPG (Highly Ordered Pyrolytic Graphite) can be used to broaden this reflection spectrum.

In the following, the image processing scheme applied according to this first embodiment according to the present invention shall be explained in more detail.

FIG. 3 shows diagrams illustrating various spectra and absorption curves, wherein E is the (photon) energy, I is the intensity of signal level and μ is the X-ray attenuation/absorption. FIG. 3a shows a conventional output spectrum of an X-ray tube. FIG. 3b shows the related transmitted beam spectrum having a dip in the spectrum due to the missing reflected X-rays. By changing the angle of the Bragg filter 14 the position of the dip can be modified as show in FIG. 3c.

According to the first embodiment of the present invention two consecutive measurements with different Bragg reflection angles of the Bragg filter are performed. While it would be ideal to perform these two measurements at the same projection angle, in practice the gantry is generally rotating continuously so that the X-ray source 2 rotates by a certain angle between the first measurement (with the first Bragg reflection angle) and the second measurement (with the second Bragg reflection angle). Hence, in practice two subsequent measurements are made from only substantially the same projection angles due to this fact. In a practical CT system approximately 1100 measurements can be made per rotation so that the difference angle between two subsequent measurements is approximately 0.33°. This is merely an example, because other CT systems may have other numbers.

This fact, which might lead to small image artifacts, can be accounted for by various measures. For instance, an interpolation can be applied on the second measurements (made with the second Bragg reflection angle) so that these measurements are interpolated on projection angles being identical to the projection angles under which the first measurements are made (with the first Bragg reflection angle). For the subsequent image processing the first measurements and the interpolated second measurement are then used. An alternative measure is to change the focal spot of the X-ray source 2 for the first and/or second measurements so that the radiation beams of two subsequent measurements are overlapping as much as possible. However, further measure generally known in the art can be applied as well.

Figure 3A:
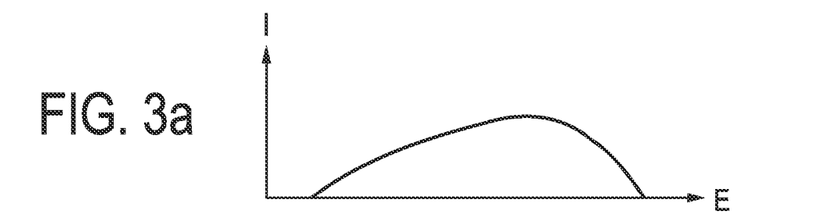
FIG. 3 shows diagrams illustrating various spectra and attenuation curves for explaining the invention.
Figure 3B:
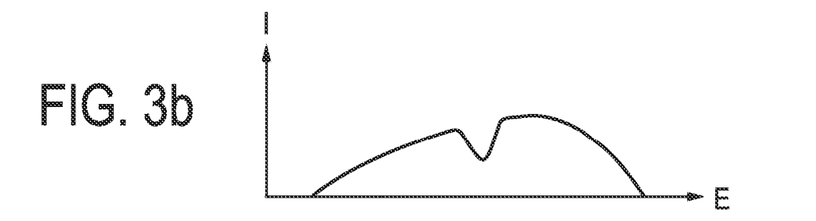
Figure 3C:
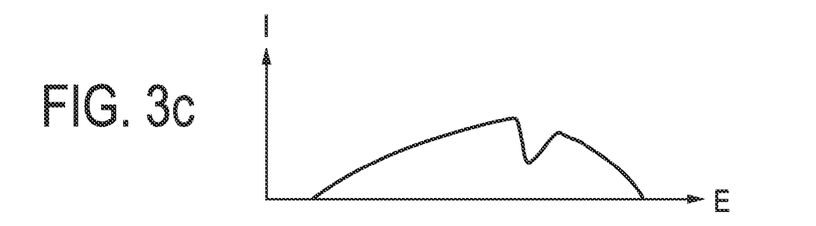
Figure 3D:
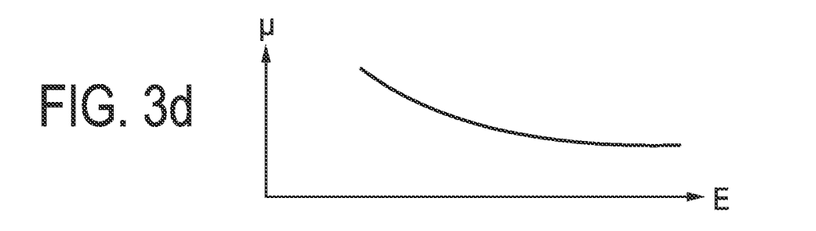
Figure 3E:
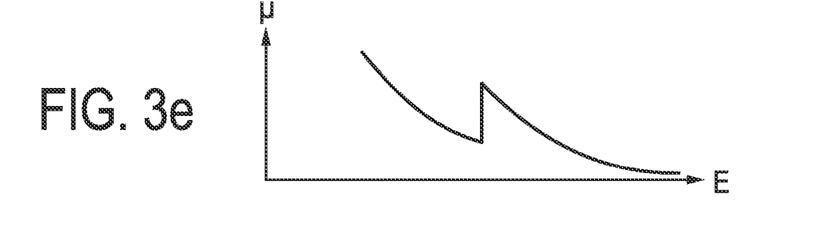

The dips in the spectrums are preferably selected such that they are on both sides of the k-edge energy from the contrast material used (e.g. Gd). The absorption curve of such a material is shown in FIG. 3e. It contains a sudden increase of the attenuation at the k-edge. Other elements in the beam without a k-edge in the energy regime have a smooth attenuation curve as shown in FIG. 3d.

Figure 4:
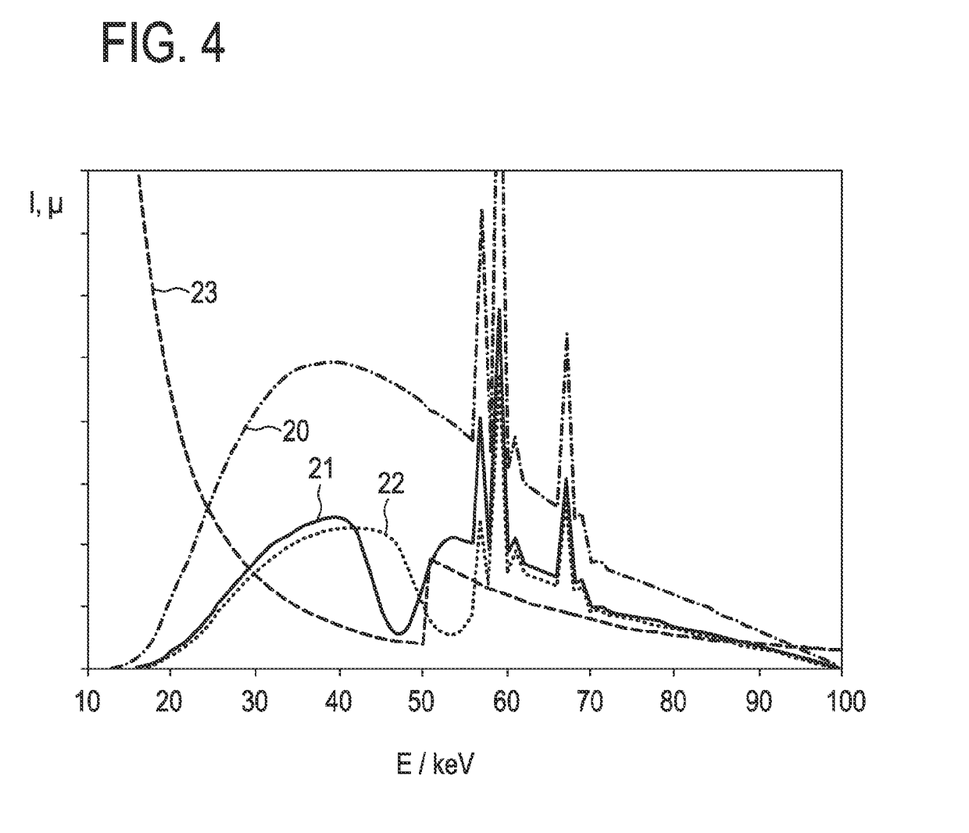
FIG. 4 shows diagrams of exemplary curves of various spectra.

FIG. 4 shows diagrams of exemplary curves for the original spectrum 20 of the X-ray source 2, the transmitted beam spectrum 21 for a first Bragg angle showing a 47 keV dip and the transmitted beam spectrum 22 for a second Bragg angle showing a 53 keV dip. The absorption curve 23 of Gd is also shown to indicate that the dips in the spectra 21, 22 are located at different sides of the k-edge.

The separation of the attenuation, resulting from the selected k-edge material is done by comparing the two (consecutive) measurements, which is done in the calculation unit 12. After a proper calibration, the k-edge related attenuation is estimated from the difference of the two measurements assuming that the difference just comes from the very different attenuation on both sides of the k-edge and that the attenuation from the other elements are the same in both measurements. If the attenuation caused by the contrast agent k-edge is known a conventional image reconstruction method can be applied by the reconstruction unit 13 to these projections to generate selective images of the contrast agent.

The measurement M of one detector element during one integration period can be approximated with:

$$M \approx \int R(E)B(E)D(E)e^{-\int \mu(e,\vec{x})ds} dE.$$

The outer integral integrates over the energy spectrum E. R(E) is the spectral density of the X-ray flux emitted from the X-ray tube during one integration period. B(E) is the effective, spectral transfer function of the Bragg filter unit. D(E) is the spectral sensitivity of the detector. The exponential function describes the attenuation in the scanned object. The argument integrates the energy (E) and spatial (x) dependent attenuation along a ray ds.

The product $R(E)B(E)D(E)=S(E)$ is combined and called the effective spectral sensitivity of the imaging device. At least two measurements are performed with different Bragg filter settings $B_1(E)$ and $B_2(E)$, and the measurements and the sensitivity are indexed accordingly $M_1$, $M_2$ and $S_1(E)$, $S_2(E)$. The integral in the exponent is inverted in the reconstruction and is not important here. It is just needed to derive the value of the integral. The integral is split into the attenuation caused by the k-edge material that shall be identified and the remaining attenuation, and the attenuation is separated into an energy dependent part and the density part:

$$\int \mu(E,\vec{x})ds = \int f(\vec{x})\phi(E)ds + \int k(\vec{x})\kappa(E)ds = F\phi(E) + K\kappa(E).$$

Together, it is obtained (equation 1):

$$M_{1,2} \approx \int S_{1,2}(E)e^{-[F\phi(E)+K\kappa(E)]} dE.$$

This formula can be used to understand the basic principle. If there is no k-edge material in the beam (K=0), the measures $M_1$ and $M_2$ are similar, because $\phi(E)$ is similar at the two centre energies ($E_{B1}$, $E_{B2}$) of the Bragg filter $\phi(E_{B1}) \sim \phi(E_{B2})$. If k-edge material is in the beam (K>0), the similarity is disturbed because $\kappa(E_{B1})$ and $\kappa(E_{B2})$ are different because of the k-edge between $E_{B1}$ and $E_{B2}$.

A number of methods can be used to obtain k-edge images from the measured data. One way is to use the formula in equation 1, to obtain the system sensitivities $S_1$ and $S_2$ and to approximate the energy dependent attenuation $\phi(E)$. Since $\kappa(E)$ is well known, a system of two non-linear equations and two unknowns F and K is obtained. Well known numerical methods can be used to find solutions. If F and K are known, conventional reconstruction techniques can be used to calculate the related images.

Another way is to perform a system calibration on the basis of well defined phantoms. For a number of known F and K combinations $(F_i, K_i)$ measurements can be done to get $M_{1,2}$ $(F_i, K_i)$. This system characteristics matrix can be used to invert measures to related attenuation values (F, K).

Another embodiment of the present invention, which uses basically the same hardware as shown in FIG. 1, performs the comparison of the measurement in the image domain. According to this embodiment first projection data from different projection angles are obtained at a first Bragg reflection angle, for instance during a first rotation of the gantry, and second projection data from different projection angles (ideally the same projection angles at which the first projection data are obtained) are obtained at a second Bragg reflection angle, for instance during a second rotation of the gantry.

A reconstruction of the two measurements $M_{1,2}$ is then performed, and the two reconstructed images can be analyzed on a pixel by pixel basis. The imaging method can either be calibrated as described for the projection analysis with measurements of well known phantoms or a simple subtraction of the images can be done. Simple image subtraction techniques show very good results.

Figure 5:
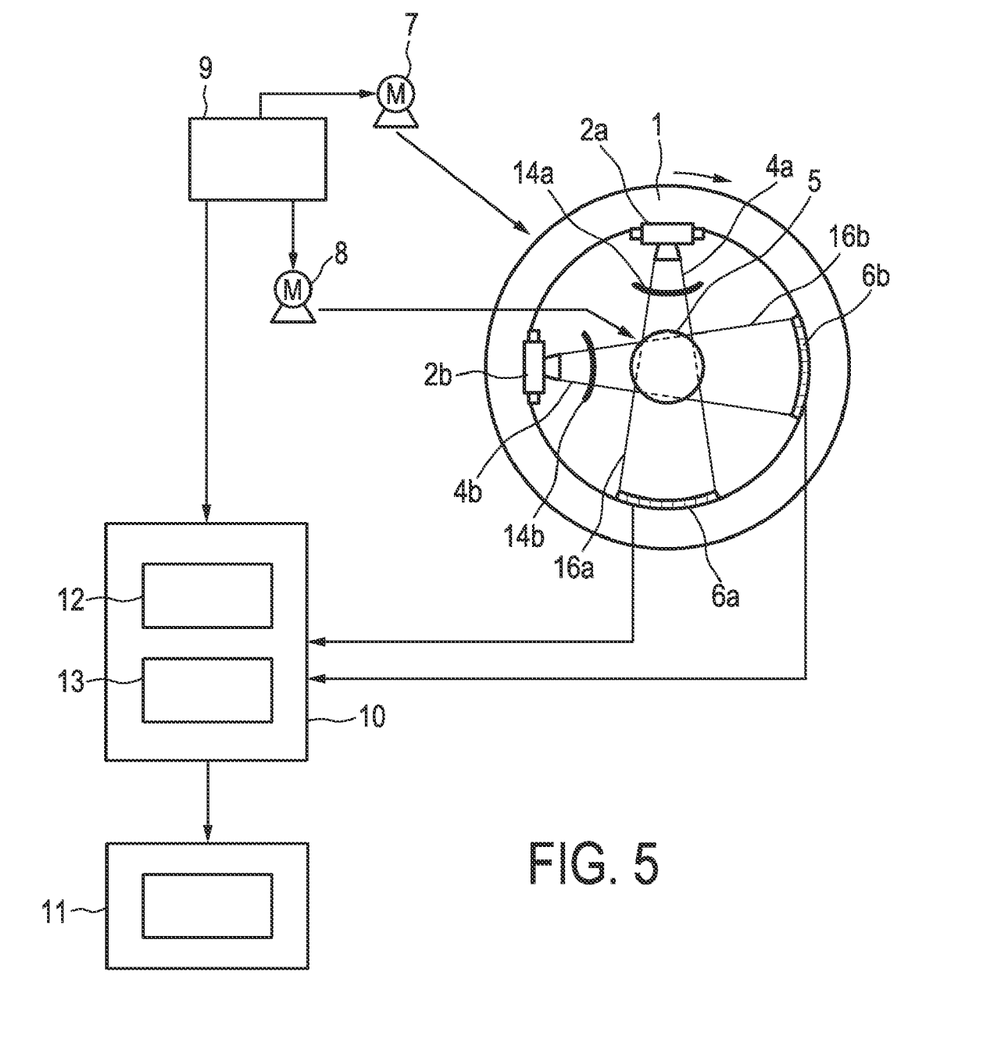
FIG. 5 shows a second embodiment of a medical X-ray examination apparatus according to the present invention.

FIG. 5 shows a further embodiment of medical X-ray examination apparatus according to the present invention. Different from the embodiment shown in FIG. 1, the apparatus now comprises two polychromatic X-ray sources 2a, 2b mounted on the gantry 1 and two corresponding X-ray detectors 6a, 6b. In this embodiment the X-ray sources 2a, 2b are mounted on the gantry 1 such that the emitted radiation beams 4a, 4b are angularly displaced by 90°, which is, however, not an essential feature; other angular displacements can be selected as well.

Further, in each radiation beam 4a, 4b between the X-ray source 2a, 2b and the object 5 a Bragg filter 14a, 14b is placed having a fixed (but different) Bragg reflection angle. Preferably, the Bragg reflection angles are selected such that the transmitted beam spectrum shows a dip as shown in FIGS. 3b, 3c, i.e. the spectrum of one of the transmitted radiation beams has a dip before the k-edge of the k-edge material present in the object and the spectrum of the other transmitted radiation beam has a dip after the k-edge of said k-edge material. Thus, with this embodiment the two sets of projection data to be obtained at different Bragg reflection angles are obtained simultaneously by the two X-ray detectors 6a, 6b. No means for controlling the Bragg reflection angles of the Bragg filters 14a, 14b are thus required in this embodiment. The further processing of the obtained projection data and the image processing steps are generally identical as explained above for the embodiment of the apparatus shown in FIG. 1. In particular, the projection data obtained at (substantially) the same projection angle but at different Bragg reflection angles can be compared first before the image processing for obtaining the k-edge image is performed. Alternatively, in a first step images are reconstructed, in particular a first image is reconstructed from the projection data obtained by the first detector 6a and a second image is reconstructed from the protection data obtained by the second detector 6b. Thereafter the reconstructed images are compared, e.g. subtracted from each other, to obtain the desired k-hatch image.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

A computer program for implementing the examination method and/or controlling the examination apparatus according to the present invention may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A medical X-ray examination apparatus for performing k-edge imaging of an object of interest including material showing k-edge absorption, comprising:
    a polychromatic X-ray source for emitting polychromatic X-ray radiation,
    a Bragg filter provided in the radiation path between said X-ray source and said object such that radiation transmitted through said Bragg filter passes through said object,
    a filter control unit for controlling the Bragg reflection angle of said Bragg filter,
    an X-ray detector for detecting X-ray radiation after passing through said object,
    an acquisition control unit for controlling the X-ray source, the X-ray detector and the filter control unit so as to acquire projection data using X-ray radiation transmitted through the Bragg filter at least two different Bragg reflection angles of said Bragg filter, and
    an image processing unit for reconstructing a k-edge image from the acquired projection data.

2. The medical X-ray examination apparatus as claimed in claim 1, wherein said an acquisition control unit is adapted for controlling the X-ray source, the X-ray detector and the filter control unit so as to acquire projection data from different projection angles, wherein from substantially the same projection angle two sets of projection data are acquired at different Bragg reflection angles of said Bragg filter, and wherein said imaging unit comprises:
    a calculation unit for determining k-edge related projection data at said different Bragg reflection angles from the difference between said two sets of projection data acquired at substantially the same projection angle, and
    a reconstruction unit for reconstructing a k-edge image from said k-edge related projection data.

3. The medical X-ray examination apparatus as claimed in claim 1, wherein said imaging unit comprises:
    a reconstruction unit for reconstructing a first image from the projection data acquired at a first Bragg reflection angle and a second image from the projection data acquired at a second Bragg reflection angle, and
    a calculation unit for determining a k-edge image from the difference between said first and second images.

4. The medical X-ray examination apparatus as claimed in claim 1, wherein said acquisition control unit is adapted for controlling said filter control unit such that the two different Bragg reflection angles used during the acquisition of the two sets of projection data result in reflected radiation, the radiation reflected at a first Bragg reflection angle having a photon energy higher than a k-edge energy of a contrast agent present in the object and the radiation reflected at a second Bragg reflection angle having a photon energy lower than a k-edge energy of said contrast agent.

5. The medical X-ray examination apparatus as claimed in claim 1, wherein said filter control unit is adapted for controlling the position and/or orientation of said Bragg filter to control said Bragg reflection angle.

6. The medical X-ray examination apparatus as claimed in claim 5, wherein said filter control unit comprises an actuator for controlling the position and/or orientation of said Bragg filter.

7. The medical X-ray examination apparatus as claimed in claim 1, wherein said filter control unit is adapted for controlling the angle between said Bragg filter and said X-ray radiation emitted from said X-ray source.

8. The medical X-ray examination apparatus as claimed in claim 1, wherein said Bragg filter is curved.

9. The medical X-ray examination apparatus as claimed in claim 1, wherein said Bragg filter is a highly oriented pyrolytic graphite (HOPG) filter.

10. A medical X-ray examination apparatus for performing k-edge imaging of an object of interest including material showing k-edge absorption, comprising:
    two polychromatic X-ray sources for emitting polychromatic X-ray radiation,
    two Bragg filters having different Bragg reflection angles, each of said Bragg filters being provided in a radiation path between one of said X-ray sources and said object such that radiation transmitted through said Bragg filters passes through said object,
    two X-ray detectors for detecting X-ray radiation after passing through said object,
    an acquisition control unit for controlling the X-ray sources and the X-ray detectors so as to acquire projection data from different projection angles, and
    an image processing unit for reconstructing a k-edge image from the acquired projection data.

11. The medical X-ray examination apparatus as claimed in claim 10, wherein said an acquisition control unit is adapted for controlling the X-ray sources and the X-ray detectors so as to acquire projection data from different projection angles, wherein from substantially the same projection angle two sets of projection data are acquired by the two X-ray detectors, and wherein said imaging unit comprises:
    a calculation unit for determining k-edge related projection data at said different Bragg reflection angles from the difference between said two sets of projection data acquired at substantially the same projection angle, and
    a reconstruction unit for reconstructing a k-edge image from said k-edge related projection data.

12. The medical X-ray examination apparatus as claimed in claim 10, wherein said imaging unit comprises:
    a reconstruction unit for reconstructing a first image from the projection data acquired by the first X-ray detector and a second image from the projection data acquired by the second X-ray detector, and
    a calculation unit for determining a k-edge image from the difference between said first and second images.

13. The medical X-ray examination apparatus as claimed in claim 10, wherein each Bragg filter is curved.

14. The medical X-ray examination apparatus as claimed in claim 10, wherein said Bragg filter is a highly oriented pyrolytic graphite (HOPG) filter.

15. A medical X-ray examination method for performing k-edge imaging of an object of interest including material showing k-edge absorption, comprising the steps of:
    emitting polychromatic X-ray radiation,
    Bragg filtering said polychromatic X-ray radiation by a Bragg filter such that radiation transmitted through said Bragg filter passes through said object,
    detecting X-ray radiation after passing through said object,
    acquiring projection data using X-ray radiation transmitted through the Bragg filter at least two different Bragg reflection angles of said Bragg filter, and
    reconstructing a k-edge image from the acquired projection data.

16. The medical X-ray examination method as claimed in claim 15, wherein said projection data is acquired from different projection angles, wherein from substantially the same projection angle two sets of projection data are acquired at different Bragg reflection angles of said Bragg filter, and wherein said method further comprises:

determining k-edge related projection data at said different Bragg reflection angles from the difference between said two sets of projection data acquired at substantially the same projection angle, and reconstructing a k-edge image from said k-edge related projection data.

17. The medical X-ray examination method as claimed in claim 15, further comprising:

reconstructing a first image from the projection data acquired at a first Bragg reflection angle and a second image from the projection data acquired at a second Bragg reflection angle, and determining a k-edge image from the difference between said first and second images.

18. The medical X-ray examination method as claimed in claim 15, wherein said at least two different Bragg reflection angles used during the acquisition of the two sets of projection data result in reflected radiation, wherein the radiation reflected at a first Bragg reflection angle having a photon energy higher than a k-edge energy of a contrast agent present in the object and the radiation reflected at a second Bragg reflection angle having a photon energy lower than a k-edge energy of said contrast agent.

19. A computer program stored on a non-transitory computer readable medium comprising program code means for controlling a medical X-ray examination apparatus which when executed on a processor performs k-edge imaging of an object of interest including material showing k-edge absorption, comprising:

a polychromatic X-ray source for emitting polychromatic X-ray radiation, a Bragg filter provided in the radiation path between said X-ray source and said object such that radiation transmitted through said Bragg filter passes through said object, a filter control unit for controlling the Bragg reflection angle of said Bragg filter, an X-ray detector for detecting X-ray radiation after passing through said object, an acquisition control unit for controlling the X-ray source, the X-ray detector and the filter control unit so as to acquire projection data at least two different Bragg reflection angles of said Bragg filter, and an image processing unit for reconstructing a k-edge image from the acquired projection data to perform the steps of the medical X-ray examination method as claimed in claim 13.

20. The computer program as claimed in claim 19, wherein the apparatus further comprises:

a reconstruction unit for reconstructing a first image from the projection data acquired at a first Bragg reflection angle and a second image from the projection data acquired at a second Bragg reflection angle, and a calculation unit for determining a k-edge image from the difference between said first and second images.

* * * * *